United States Patent
Wei et al.

(10) Patent No.: US 10,379,045 B2
(45) Date of Patent: Aug. 13, 2019

(54) LABEL-FREE SENSING CHIP AND APPLICATION THEREOF

(71) Applicant: Academia Sinica, Taipei (TW)

(72) Inventors: Pei-Kuen Wei, Taipei (TW); Kuang-Li Lee, Taipei (TW)

(73) Assignee: ACADEMIA SINICA, Taipei (TW)

( * ) Notice: Subject to any disclaimer, the term of this patent is extended or adjusted under 35 U.S.C. 154(b) by 841 days.

(21) Appl. No.: 14/476,191

(22) Filed: Sep. 3, 2014

(65) Prior Publication Data

US 2015/0080253 A1 Mar. 19, 2015

Related U.S. Application Data

(60) Provisional application No. 61/878,662, filed on Sep. 17, 2013.

(51) Int. Cl.
*G01N 21/59* (2006.01)

(52) U.S. Cl.
CPC ..... *G01N 21/59* (2013.01); *G01N 2021/5903* (2013.01)

(58) Field of Classification Search
CPC ...... G02B 5/008; G02B 1/002; G02B 6/1226; G01N 21/554; G01N 21/3577; G01N 21/6452; G01N 33/553
See application file for complete search history.

(56) References Cited

U.S. PATENT DOCUMENTS

| | | | |
|---|---|---|---|
| 7,708,945 B1* | 5/2010 | Abel | C12Q 1/6816 422/430 |
| 2004/0248318 A1* | 12/2004 | Weinberger | B01L 3/502715 436/173 |
| 2006/0273245 A1 | 12/2006 | Kim et al. | |
| 2009/0181857 A1 | 7/2009 | Wei et al. | |
| 2014/0268332 A1* | 9/2014 | Guo | G02B 5/008 359/487.01 |

OTHER PUBLICATIONS

Lee et al "Improving surface plasmon detection in gold nanostructures using a multi-polarization spectral integration method", Adv. Mater, Jun. 16, 2012, 24: OP253-OP259. (Year: 2012).*
Homola, Surface plasmon resonance sensors: review, Sensors and Actuators B 54, 1999, pp. 3-15, Elsevier Science S.A.

(Continued)

*Primary Examiner* — Betty J Forman
(74) *Attorney, Agent, or Firm* — Bacon & Thomas, PLLC

(57) ABSTRACT

The present invention provides a label-free sensing chip for identifying a chemical substance, comprising: (a) a transparent substrate comprising a base and first periodic ridges; and (b) a metal layer covering said transparent substrate, comprising second periodic ridges and third periodic ridges, in which said second periodic ridges has a height equal to or greater than the height of the first periodic ridges, and each ridge of the second periodic ridges fits into the space between each ridge of the first periodic ridges, and said third periodic ridges correspondingly located on said first periodic ridges. The present invention also provides a method for identifying a chemical substance by using the foresaid label-free sensing chip.

20 Claims, 9 Drawing Sheets

(56) References Cited

OTHER PUBLICATIONS

Ebbesen, Extraordinary optical transmission through sub-wavelength hole arrays, Nature, date Feb. 12, 1998, vol. 391, Macmillan Publishers Ltd.
Brolo, Surface Plasmon Sensor Based on the Enhanced Light Transmission through Arrays of Nanoholes in Gold Films, Langmuir, date 2004, vol. 20, pp. 4813-4815, Published on Web May 5, 2004, American Chemical Society.
Lee, Sensitive biosensor array using surface plasmon resonance on metallic nanoslits, Journal of Biomedical Optics 12(4), 044023, date Jul./Aug. 2007, published online Aug. 31, 2007, SPIE.
Lee, Enhancing Surface Plasmon Detection Using Template-Stripped Gold Nanoslit Arrays on Plastic Films, Published online Mar. 27, 2012, American Chemical Society.
Anker, Biosensing with plasmonic nanosensors, Nature Materials, vol. 7, date Jun. 2008, Nature Publishing Group.
Stewart, Nanostructured Plasmonic Sensors, Chem. Rev. 2008, 108, 494-521, Published on Jan. 30, 2008, American Chemical Society.
Miroshnichenko, Fano resonances in nanoscale structures, Reviews of Modern Physics, vol. 82, date Jul.-Sep. 2010, Published Aug. 11, 2010, The American Physical Society.
Luk'Yanchuk, The Fano resonance in plasmonic nanostructures and metamaterials, Nature Materials, vol. 9, date Sep. 2010, Published online: Aug. 23, 2010; 2010 Macmillan Publishers Limited.

\* cited by examiner

LABEL-FREE SENSING CHIP AND APPLICATION THEREOF

BACKGROUND OF THE INVENTION

Field of the Invention

The present invention is related to a label-free sensing chip and applications thereof, especially, a method for identifying a chemical substance by using the label-free sensing chip.

Description of the Related Art

The study and development of biochips, such as DNA microarrays, lab on a chip, protein microarrays and carbohydrate chips, have the potential to benefit numerous important fields including medical diagnostics, pharmaceutical research, environmental monitoring, plant pathogen detection and food safety. Fluorescent labeling and the enzymatic colorimetric method are widely used in microarrays. When labeled targets interact with the probes on the microarray, the bio-affinities between targets and specific probes are read from the fluorescent intensity or colors of the spots on the chips. However, these labeling techniques have some drawbacks, including high cost and complicated labeling processes.

In order to solve the problems of the mentioned techniques, surface plasmon resonance (SPR), which can be applied for label-free and highly sensitive detection, provides a good way to develop label-free biochips. Such sensing technique has been widely applied for measuring antigen-antibody binding affinities. The common approach employs attenuated total reflection (ATR) in a glass prism to excite a surface plasmon wave (SPW) on a 50-nm-thick gold film coated on the prism. When biomolecules are adsorbed on the metal surface, the reflected light signal changes. ATR biosensors are known to be very sensitive to surface environmental changes. However, due to its optical configuration, it is hard to be applied for high-throughput and chip-based detections, such as DNA and protein microarrays.

In addition to the prism coupling method, the SPR can also be excited using metallic nanostructures. In 2004, chip-based SPR biosensors based on extraordinary transmissions of periodic gold nanohole arrays was proposed (see FIG. 1(a)). Besides, nanoslit-based SPR sensors (see FIG. 1(b)) and nanoparticle-based localized surface plasmon resonance (LSPR) sensors were reported. Compared to the prism-based SPR sensors, the gold nanostructures benefit from having a small detection volume, small detection area and simple optical measuring system in a transmission mode or reflection mode. They provide a feasible way to achieve the goal of chip-based, high-throughput and label-free detection.

SUMMARY OF THE INVENTION

The object of the present invention is to develop a label-free sensing chip for identifying a chemical substance based on Fano resonance. Fano resonance provides an asymmetric and narrow bandwidth of resonance, which enhances the sensing sensitivities of SPR sensors and effectively improves the sensing resolution of chemical substances, such as biomolecules.

Another object of the present invention is to provide a method for identifying a chemical substance by using the foresaid label-free sensing chip.

Accordingly, the present invention provides a label-free sensing chip for identifying a chemical substance, comprising: a transparent substrate comprising a base and first periodic ridges; and a metal layer covering said transparent substrate, comprising second periodic ridges and third periodic ridges, in which said second periodic ridges has a height equal to or greater than the height of the first periodic ridges, and each ridge of the second periodic ridges fits into the space between each ridge of the first periodic ridges, and said third periodic ridges correspondingly located on said first periodic ridges.

In preferred embodiments of the present invention, said label-free sensing chip further comprises a molecule layer coated on the metal layer, wherein said molecule layer comprises one or more molecules for binding the chemical substance.

In preferred embodiments of the present invention, said chemical substance comprises elements, biomolecules, polymers and drugs; more preferably, said biomolecules comprise proteins, DNA and RNA.

In preferred embodiments of the present invention, said third periodic ridges has a height equal to or less than the height of the second periodic ridges; more preferably, said third periodic ridges has a height equal to the height of the second periodic ridges.

In preferred embodiments of the present invention, said second periodic ridges have a height of several tens nm to several hundred nm.

In preferred embodiments of the present invention, said second periodic ridges have a period (P) of several hundred nm to several μm; more preferably, each ridge of said first periodic ridges has a width (w) of 10 nm to 200 nm. The length of said first periodic ridges is not specifically limited, but it is generally greater than 1 μm; preferably, greater than several μm.

In preferred embodiments of the present invention, said transparent substrate is composed of glass or a plastic material; more preferably, said plastic material selected from acrylic, UV gel, polycarbonate or cyclo olefin polymers; most preferably, said plastic material is polycarbonate.

In preferred embodiments of the present invention, said metal layer is composed of the metal selected from gold, silver, aluminum or copper; more preferably, said metal is gold.

The present invention provides a method for identifying a chemical substance, comprising:
(a) providing a sample of said chemical substance;
(b) adding said sample on the above-mentioned label-free sensing chip to cover the metal layer;
(c) transmitting an incident light from the substrate side;
(d) detecting the transmission spectra of the sample to identify the chemical substance.

In preferred embodiments of the present invention, the label-free sensing chip of the step (b) further comprises a molecule layer coated on the metal layer, and said molecule layer comprises one or more molecules for binding the chemical substance; more preferably, the method further comprises a step after said step (b): interacting the one or more molecules and the chemical substance.

In preferred embodiments of the present invention, said sample is in form of liquid or gas.

In preferred embodiments of the present invention, said chemical substance to be identified by the method comprises biomolecules; more preferably, said biomolecules comprise proteins; even more preferably, said protein is solved in a PBS buffer solution. The concentration of the chemical substance is not specifically limited.

In preferred embodiments of the present invention, said incident light is polarized; more preferably, said incident light is a TM-polarized light; more preferably, the incident angle of the TM-polarized light is from 0° to 40°. Among the measurable spectra range (400-1000 nm), the angle formed by the k vector of the incident light and the normal vector of the sensing chip is from 0° to 40°. The range of the incident angle changes according to the period. Most preferably, the incident angle of the TM-polarized light is from 0° to 40° when 500-nm-period double-layered metallic nano-ridges are used. In addition, the E vector of the TM-polarized light is perpendicular to the ridges.

In preferred embodiments of the present invention, said incident light is transmitted into the substrate in direction substantively perpendicular to the label-free sensing chip.

The present invention provides a label-free sensing chip and a method for identifying a chemical substance by using the label-free sensing chip. The metal layer of the label-free sensing chip of the present invention forms cavities to generate Fano resonances, which has high sensing sensitivity and resolution for detection of unknown chemical substances.

DETAILED DESCRIPTION OF THE PREFERRED EMBODIMENTS

Figure 1:
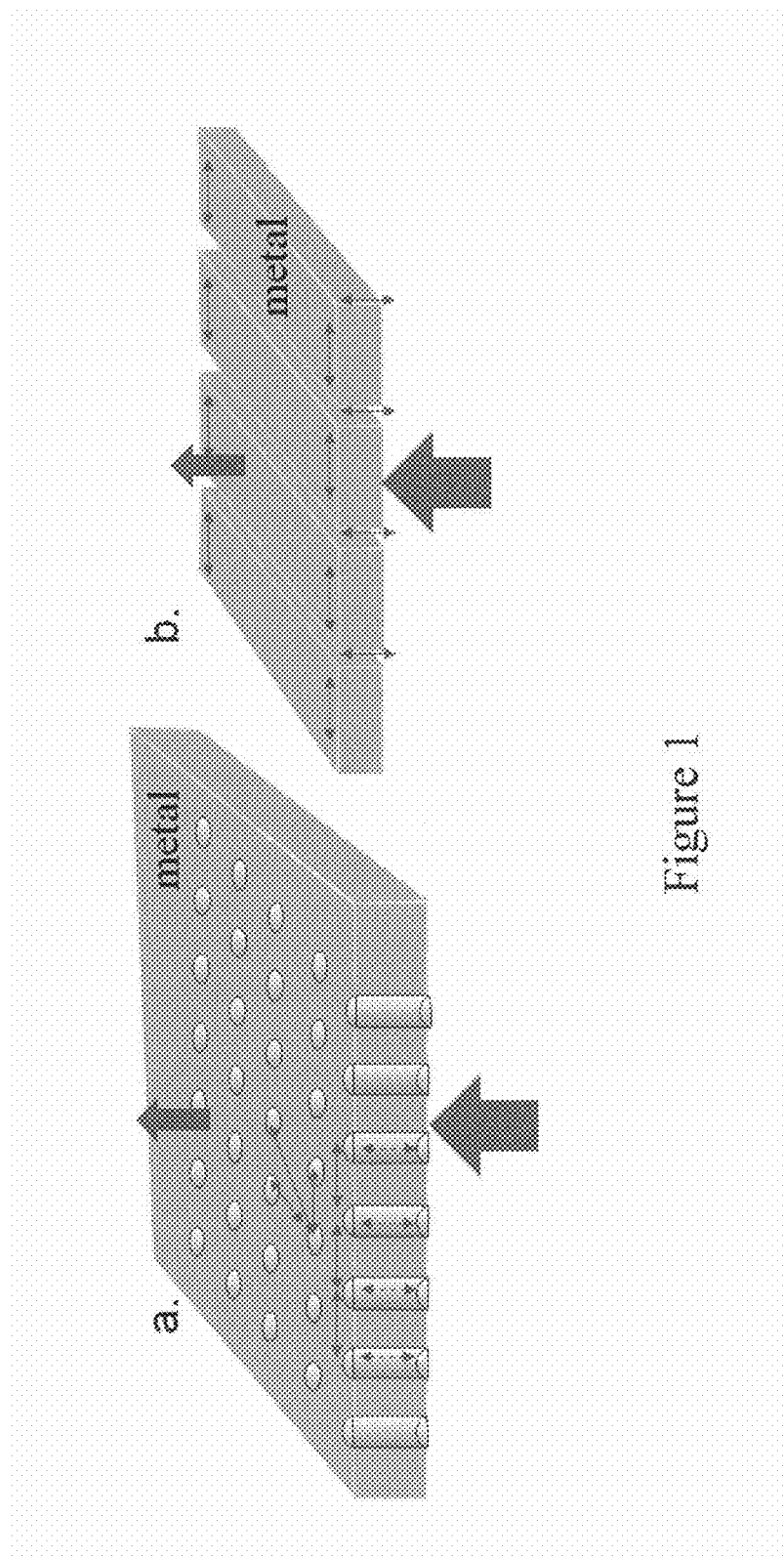
FIG. 1 shows schematic configurations of conventional periodic nanostructure-based surface plasmon resonance sensors: (a) metallic nanohole arrays and (b) metallic nanoslit arrays.
Figure 2:
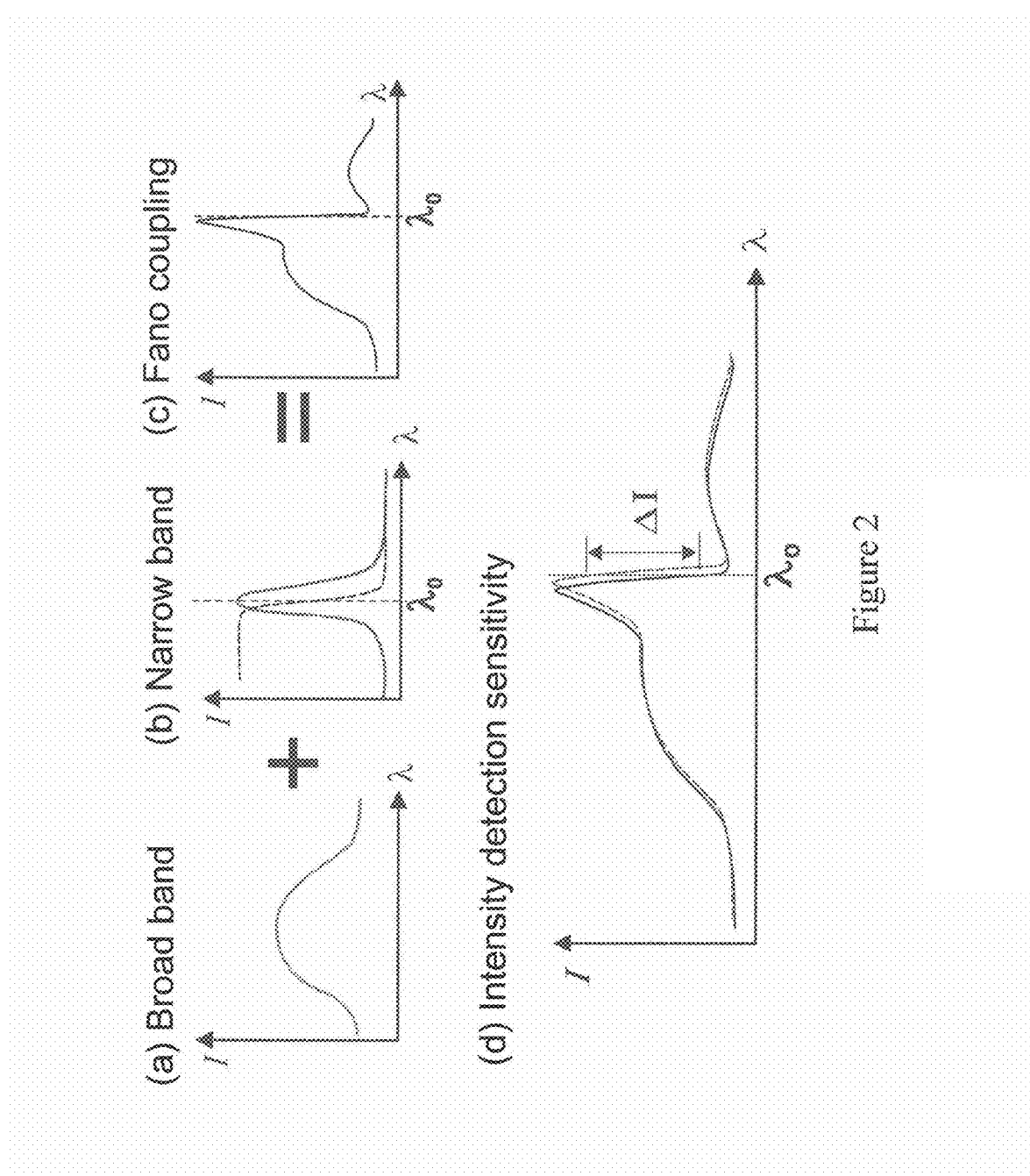
FIG. 2 schematically shows (a) broad band resonance profile generated by LSPR; (b) a narrow band resonance profile generated by BW-SPP; (c) the Fano resonance profile generated from the coupling of the broad band resonance and the narrow band resonance; and (d) the red shift of Fano resonance profile caused by chemical substance absorption.

The label-free sensing chip of the present invention is different from the conventional SPR sensors using metallic nanohole or nanoslit arrays and LSPR sensors using nanoparticles. In this invention, we utilize Fano resonances generated in the double-layered metallic nano-ridges of the present invention to enhance the sensing sensitivities of SPR sensors. As shown in FIG. 2, Fano resonance is generated from the coupling of a broad band resonance and a narrow band resonance. It has an extremely sharp and asymmetric resonance peak near the resonant wavelength, which can enhance the sensing sensitivities of SPR sensors. Fano resonance has a narrower bandwidth than other resonant systems. When chemical substances, especially biomolecules, are adsorbed on the structure surface, the resonance peak will be red shifted. The intensity change at a certain wavelength is related to the sharpness of the resonance peak, and the Fano resonance can provide a higher intensity sensitivity ($\Delta I$) due to its extremely sharp and narrow band width.

Figure 3:
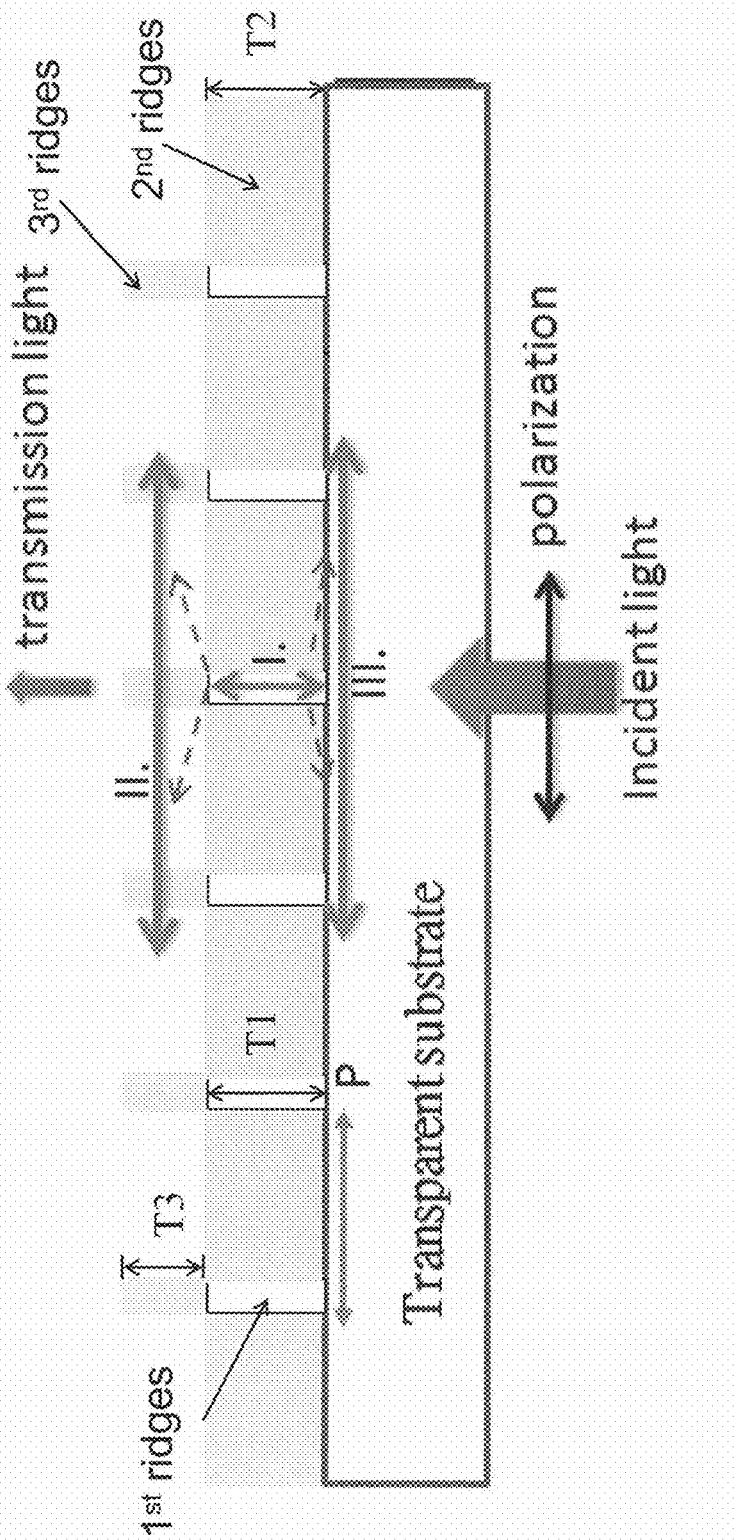
FIG. 3 shows the schematic cross-sectional view of the label-free sensing chip of the present invention.

In this invention, a structure comprising double-layered metallic nano-ridges (i.e. the metal layer) is provided, as shown in FIG. 3. This structure comprises three sets of nano-ridges, the first periodic ridges are transparent ridges composed of the material the same with the base of the substrate, having a width of w and a height of T1. The other two sets of ridges, the second and third periodic ridges, are composed of metal, in which the second periodic ridges are "engaged with" the transparent ridges: each ridge of the second periodic ridges fits into the space between each ridge of the first periodic ridges. And, the height of the second periodic ridges (T2) is the same with the height of the third periodic ridges (T3), and T2 equals to T3 in the following examples. The third periodic ridges are correspondingly located on said first periodic ridges. The period of the second periodic ridges is represented as P. Since light can pass through the transparent material but cannot pass through the metal, the two sets of metallic ridges form a series of "cavities" for the incident light, which are substantively equal to the transparent ridges. That is to say, the incident light will be captured in the cavities.

When the label-free sensing chip of the present invention is used for identifying a chemical substance, a sample solution is added on the surface of the double-layered metallic nano-ridges, and the chemical substance will be absorbed on the surface of the metal layer. The unbound chemical substance is removed by washing steps. After that, an incident light is polarized and transmitted from the substrate side in a direction perpendicular to the substrate, and localized surface plasmon resonances (LSPRs) are generated in the cavities (zone I). Also, the Bloch wave surface plasmon polaritons (BW-SPPs) separately occur on the metal/sample solution (zone II) and metal/substrate (zone III) interfaces when the Bragg condition is satisfied. The LSPR and BW-SPP generate a broad band resonance and a narrow band resonance in the transmission spectrum, respectively. They will be coupled to give a Fano resonance.

The resonant condition of the LSPRs (i.e. cavity resonances) can be estimated by the equation of Fabry-Perot cavity, $$2n_{eff}k_0 h + \phi_1 + \phi_2 = 2\pi \qquad (1)$$

where $n_{eff}$ is the equivalent refractive index in the first ridges, $k_0$ is the free space wavelength vector ($2\pi/\lambda_0$), h is the thickness of metal film (ex. gold film) or first periodic ridges and $\phi_1$ and $\phi_2$ are the phase shifts at the top and bottom interfaces. Regarding with the BW-SPPs, the condition for a 1-D array can be described by the following equation when a normally incident light is given, $$\lambda_{SPR}(n, i) = \frac{P}{i}\left(\frac{\varepsilon_m n^2}{\varepsilon_m + n^2}\right)^{1/2} \quad (2)$$

where i is the resonant order, P is the period of the nanostructure, $\varepsilon_m$ is the dielectric constant of the metal and n is the environmental refractive index. The interaction between the LSPR and BW-SPP creates a Fano resonance profile consisting of a minimum intensity, close to the position predicted by equation 2 (i.e. $\lambda_0$, the resonant wavelength), and an adjacent maximum intensity, as shown in FIG. 2(c).

Compared to the conventional periodic nanohole or nanoslit arrays, the proposed structure in the present invention generates an extremely sharp Fano resonance due to the use of the double-layered metallic nano-ridges. It increases the intensity of cavity resonances and the coupling efficiency between the LSPR and BW-SPPs.

EXAMPLES

Example 1, Preparation of the Label-Free Sensing Chip

Figure 4:
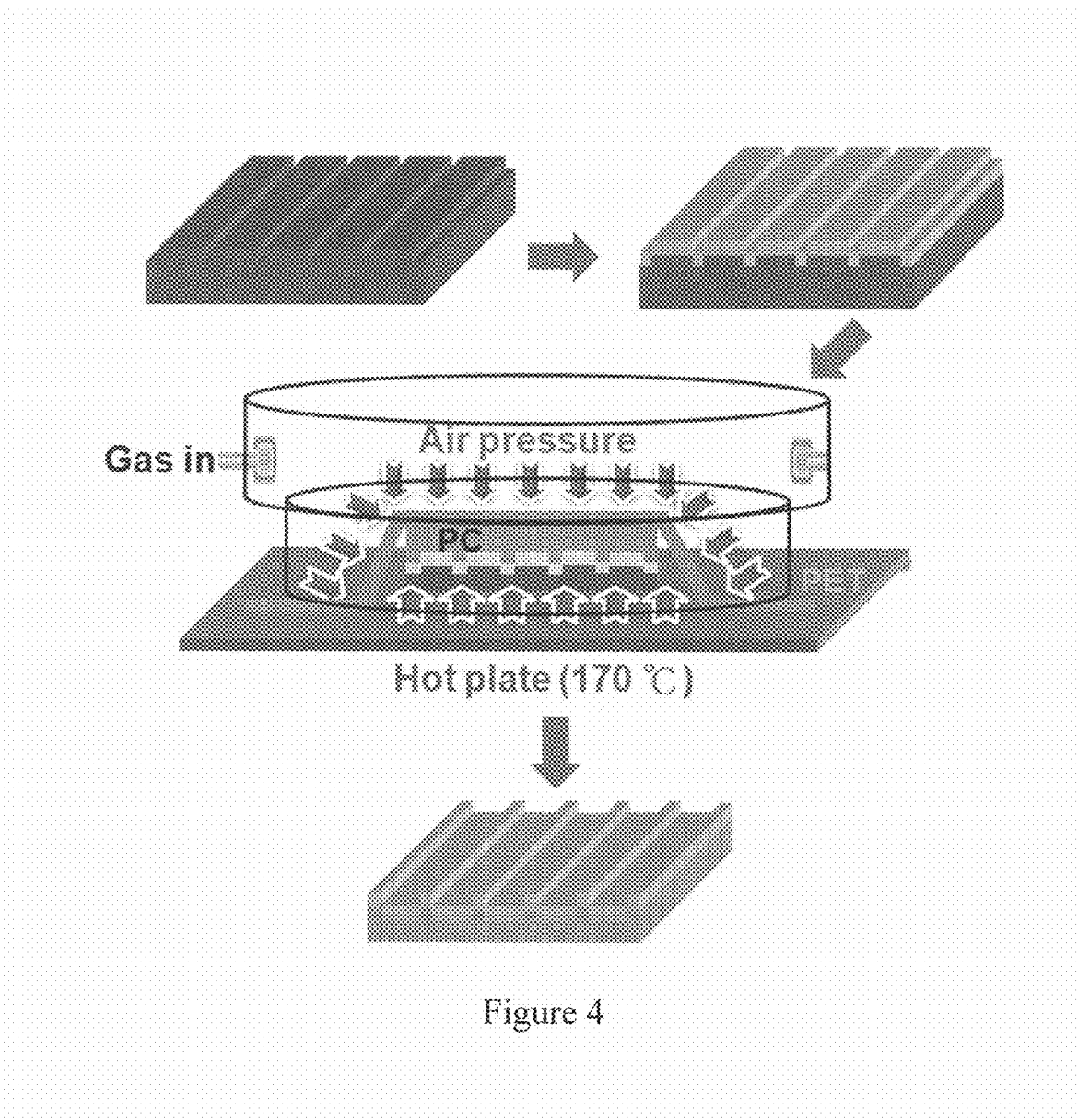
FIG. 4 schematically depicts the preparation process of the label-free sensing chip of the present invention.

The label-free sensing chip can be prepared by many processes. In this example, a thermal annealing-assisted template stripping method is applied for the preparation of the label-free sensing chip of the present invention. This process is schematically depicted in FIG. 4.

First of all, a silicon substrate was provided. E-beam lithography (EBL) and reactive ion etching (RIE) were used to fabricate the nanogrooves on the Si substrate. Gold was deposited on the Si template using an electron gun evaporator to give two sets of ridges: second and third periodic ridges, and the two sets of ridges formed gold periodic nanogrooves. The thickness of the deposited gold layer is equal or slightly greater than the depth of the nanogrooves on the Si template. In accordance with the geometrical parameters used in the present invention (see the following Table 1), the transmission rate of the incident light will decrease and fail to generate Fano resonance if the thickness of the deposited gold later is greater than the depth of the nanogrooves by about 25% or above. After that, a 178-μm-thick polycarbonate (PC) film (Lexan8010, GE, USA) was placed on the gold coated template. The template and PC substrate was placed on a heating plate. It was heated at a temperature of 170° C. to soften the PC substrate. An additional polyethylene terephthalate (PET) thin film was used as the sealing film. In the system, nitrogen gas was introduced into the chamber to produce a uniform pressure (2 kgw/cm$^2$) over the film. It pressed the silicon mold and PC substrate with large-area uniformity. This step made the gold film uniformly stuck to the softened PC film. The template and substrate were then cooled and taken out from the chamber. As the gold film had a poor adhesion to the silicon template, the PC film was easily separated from the silicon template. After peeling off from the template and PET thin film, the PC substrate with metallic nanostructures was made.

The melted polycarbonate filled into the gold periodic nanogrooves, and formed the first periodic ridges and base of the substrate. After that, the deposited gold layer was transferred onto the PC layer to give the sensing chip of the present invention. This is because the affinity (adhesion) between the gold film and Si substrate is weaker than that between the gold layer and PC layer (i.e. the substrate of the sensing chip of the present invention).

Figure 5:
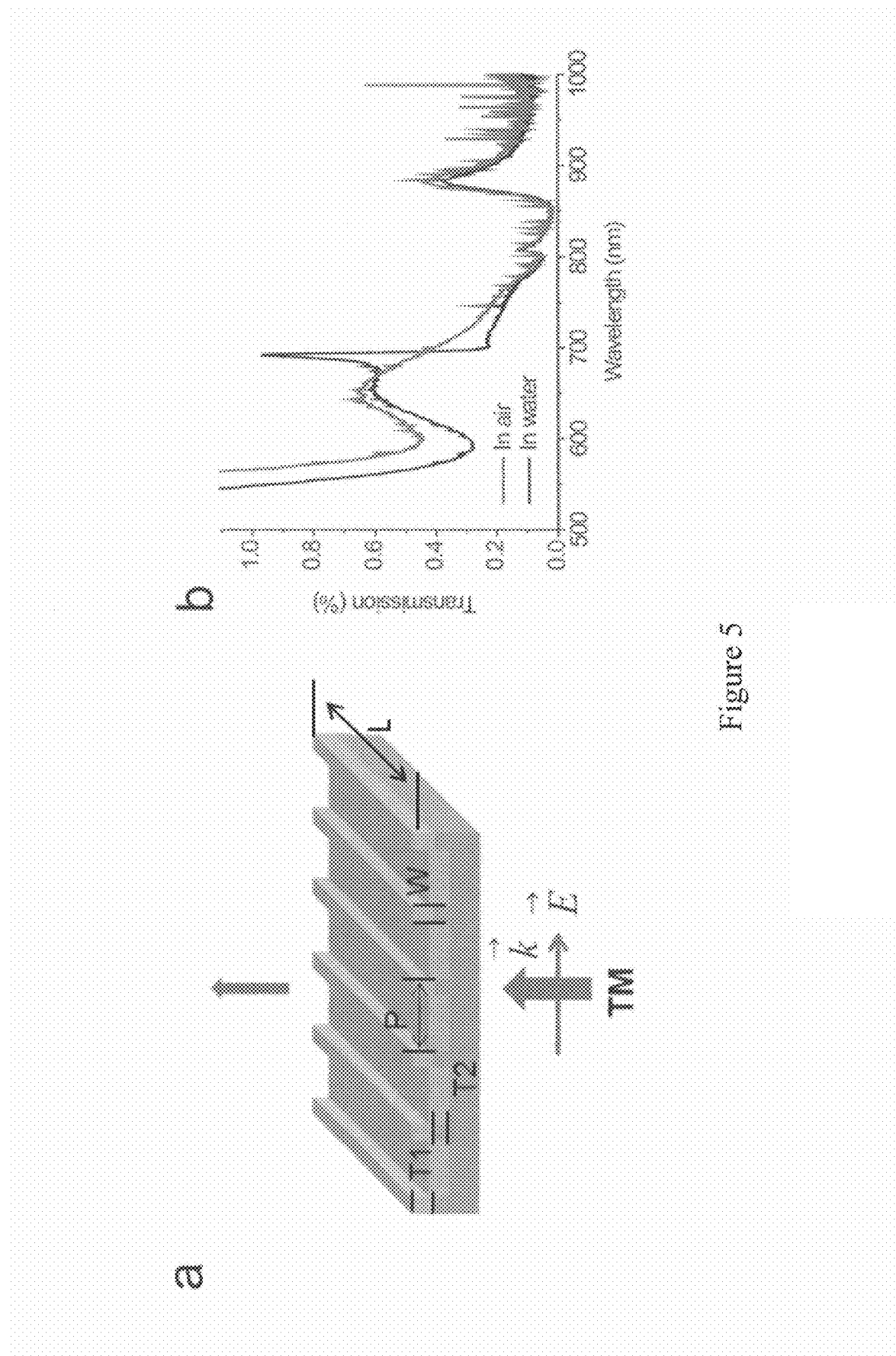
FIG. 5 shows (a) a schematic configuration depicting the geometrical parameters of the double-layered metallic nano-ridges, as well as the direction of the TM-polarized incident light with E and k vectors; (b) the measured transmission spectra of the 500-nm-period double-layered metallic nano-ridges in air and water for normally-incident TM-polarized light; (c) the transmission spectra of the double-layered metallic nano-ridges with various periods (from 500 to 650 nm) in water for a TM-polarized wave; (d) the experimental wavelengths of Fano resonances and theoretical resonance wavelengths of BW-SPPs as a function of period.
Figure 5:
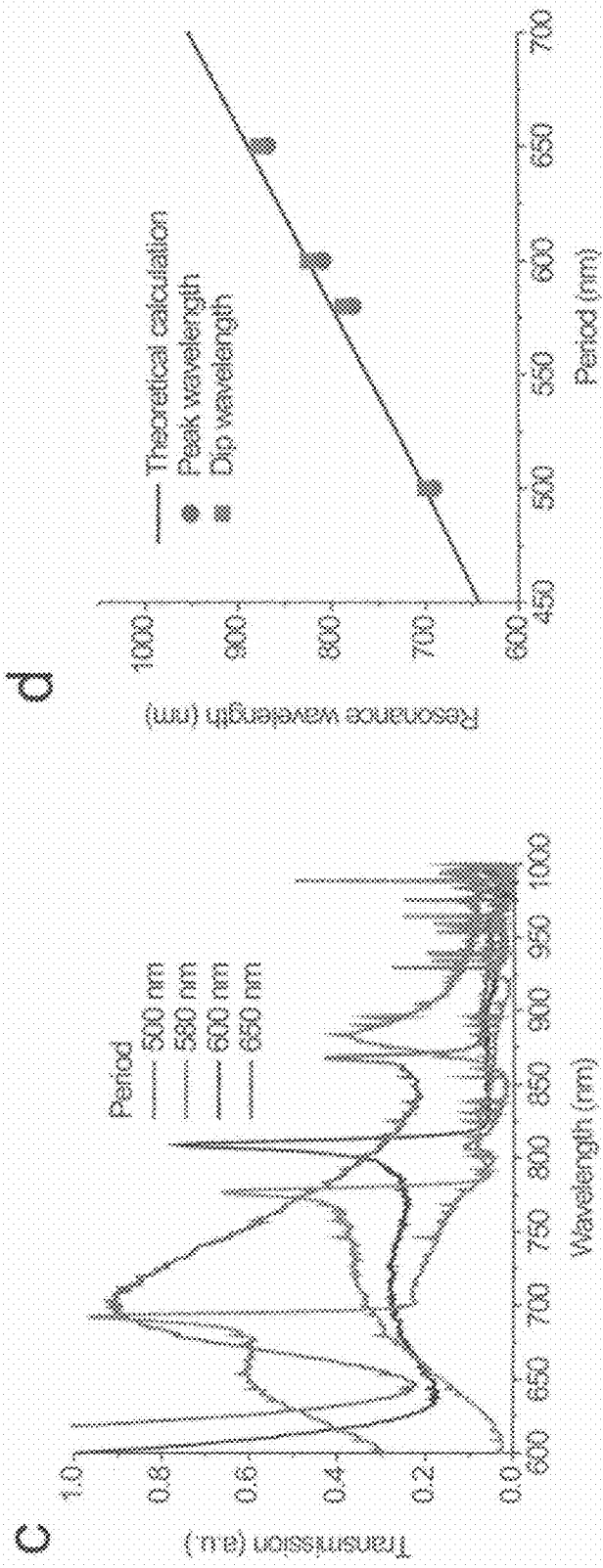

FIG. 5(a) further depicts the geometrical parameters of the double-layered metallic nano-ridges (i.e. the metal layer), as well as the direction of the TM-polarized incident light with E vector (electric field vector) and κ vector (wave vector). The geometrical parameters used in the following Examples are listed as below:

TABLE 1 the geometrical parameters of the sensing chip of the present invention

|     | P      | T1    | T2    | W      | L      |
|-----|--------|-------|-------|--------|--------|
| S1  | 500 nm | 55 nm | 80 nm | 60 nm  | 150 μm |
| S2  | 580 nm | 55 nm | 80 nm | 80 nm  | 150 μm |
| S3  | 600 nm | 55 nm | 80 nm | 80 nm  | 150 μm |
| S4  | 650 nm | 55 nm | 80 nm | 80 nm  | 150 μm |
| S5  | 500 nm | 50 nm | 80 nm | 50 nm  | 150 μm |
| S6  | 500 nm | 55 nm | 80 nm | 80 nm  | 150 μm |
| S7  | 500 nm | 55 nm | 80 nm | 90 nm  | 150 μm |
| S8  | 500 nm | 60 nm | 80 nm | 95 nm  | 150 μm |
| S9  | 500 nm | 60 nm | 80 nm | 100 nm | 150 μm |
| S10 | 500 nm | 60 nm | 80 nm | 125 nm | 150 μm |

The length of the ridges (L) was not specifically limited. The polarization of the incident light was perpendicular to the transparent PC substrate. The light transmitted from another angle also could be used, but the angle of light would change the position of the Fano resonance peak.

Example 2, Transmission Spectra of the Label-Free Sensing Chip of the Present Invention in Air and Water The transmission spectra of air (no sample) and water (blank) were measured with the label-free sensing chip with 500-nm-period metallic nano-ridges (S1) and normally-incident TM-polarized light. When a sample solution (such as water or a protein solution) was used, the sample solution was added to cover the metallic nano-ridges of the sensing chip. The transmission spectra of air and water are shown in FIG. 5(b).

FIG. 5(b) shows that there is a broad resonance near 650 nm, which is related to the cavity resonance. From equation 2, the resonant wavelength of the BW-SPP is 832 nm at the PC/gold interface (εm=−29+2.0i for gold at 800 nm, i=1, n=1.584 and P=500 nm). In FIG. 5(b), it is clear that a Fano resonance peak is present near 832 nm, in which the corresponding peak and dip wavelengths are 803 and 807 nm, respectively. The experimental wavelength was close to the theoretical wavelength.

When water is used as the sample solution, there are two Fano resonances generated in the transmission spectrum. When the chip was covered with water, there are two Fano resonance peaks present in the transmission spectrum of water, in which the resonant wavelengths at the metal/substrate (zones I+III) and metal/water interface (zones I+II) are at 807 and 692 nm, respectively. From equation 2, the resonant wavelength of the BW-SPP at the water/gold interface is 704 nm (εm=−16.8+1.1i for gold at 705 nm, i=1, n=1.3320 and P=500 nm), and the resonant dip of Fano resonance at the water/gold interface was at the wavelength of 692 nm. The experimental wavelength was close to the theoretical wavelength. As for the resonant dip of Fano resonance at the PC/gold interface, it is the same with that shown in the transmission spectrum of air.

In the following Examples, only the Fano resonance coupled by the broad band resonance of zone I and the narrow band resonance of zone II is used for the detection. That is because the Fano resonance coupled by zone I and zone III is not very sensitive to the changes of environmental refractive index. For example, the Fano resonances coupled by zone I and zone III in air and water are almost the same.

FIG. 5(c) shows the transmission spectra of the double-layer metallic nano ridges with various periods in water for a TM-polarized wave (S1~S4). The couplings of cavity resonances in ridges and BW-SPPs on the periodic ridges create Fano resonances in the spectra. Obviously, the experimental wavelengths were proportional to the periods and close to the theoretical values shown in FIG. 5(d).

Figure 6:
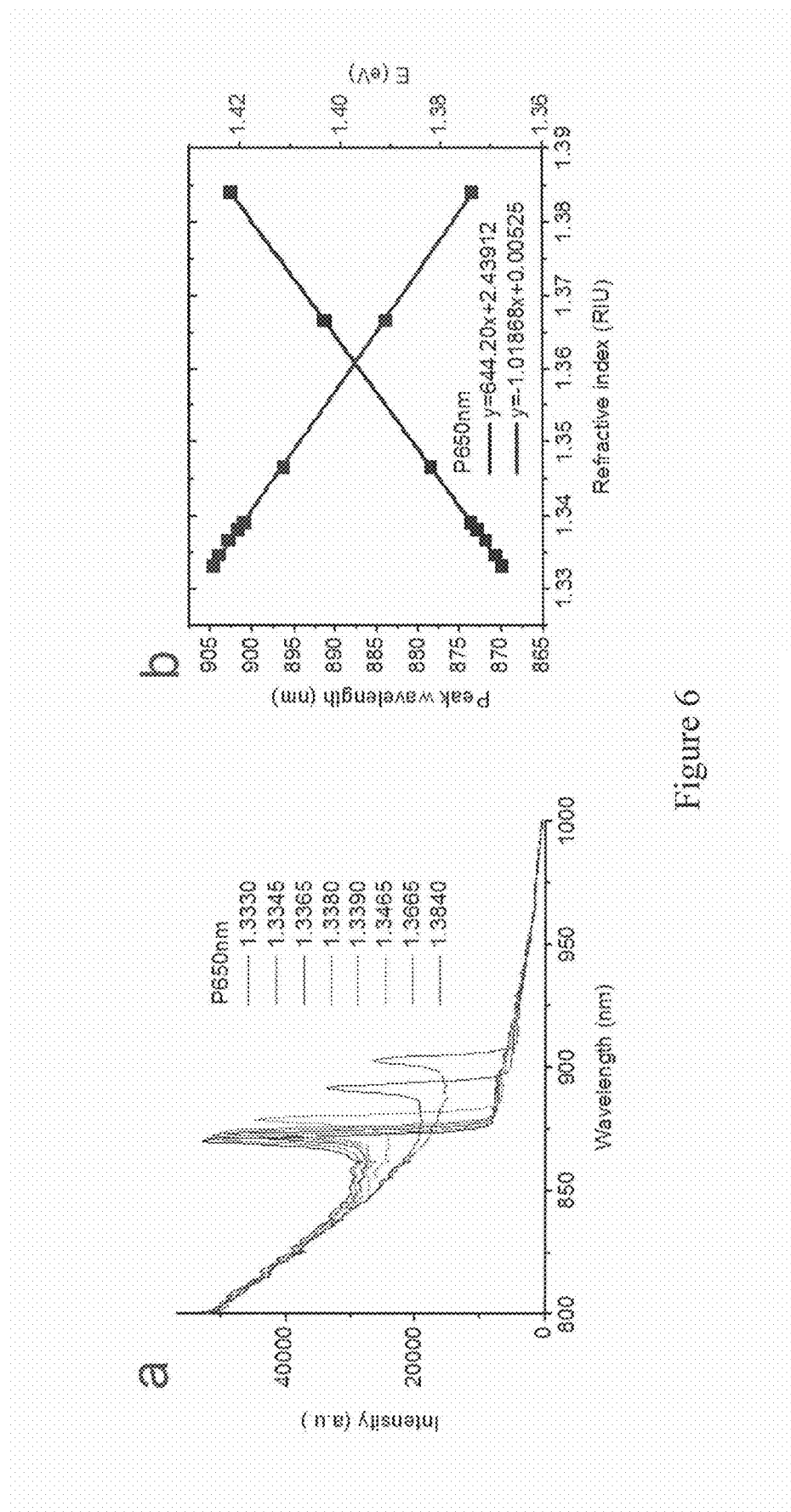
FIG. 6 shows (a) the intensity spectra of the 650-nm-period double-layered metallic nano-ridges with various water/glycerin mixtures for a normally-incident TM-polarized wave; (b) the resonant peak wavelength against the refractive index of the water/glycerin mixtures; (c) the normalized intensity change at a wavelength of 874 nm against the refractive index of the water/glycerin mixtures; (d) the enlarged intensity spectra of the 650-nm-period double-layered metallic nano-ridges in the water/glycerin mixture having an RIU value (n) of 1.3365 for a normally-incident TM-polarized wave.
Figure 6:
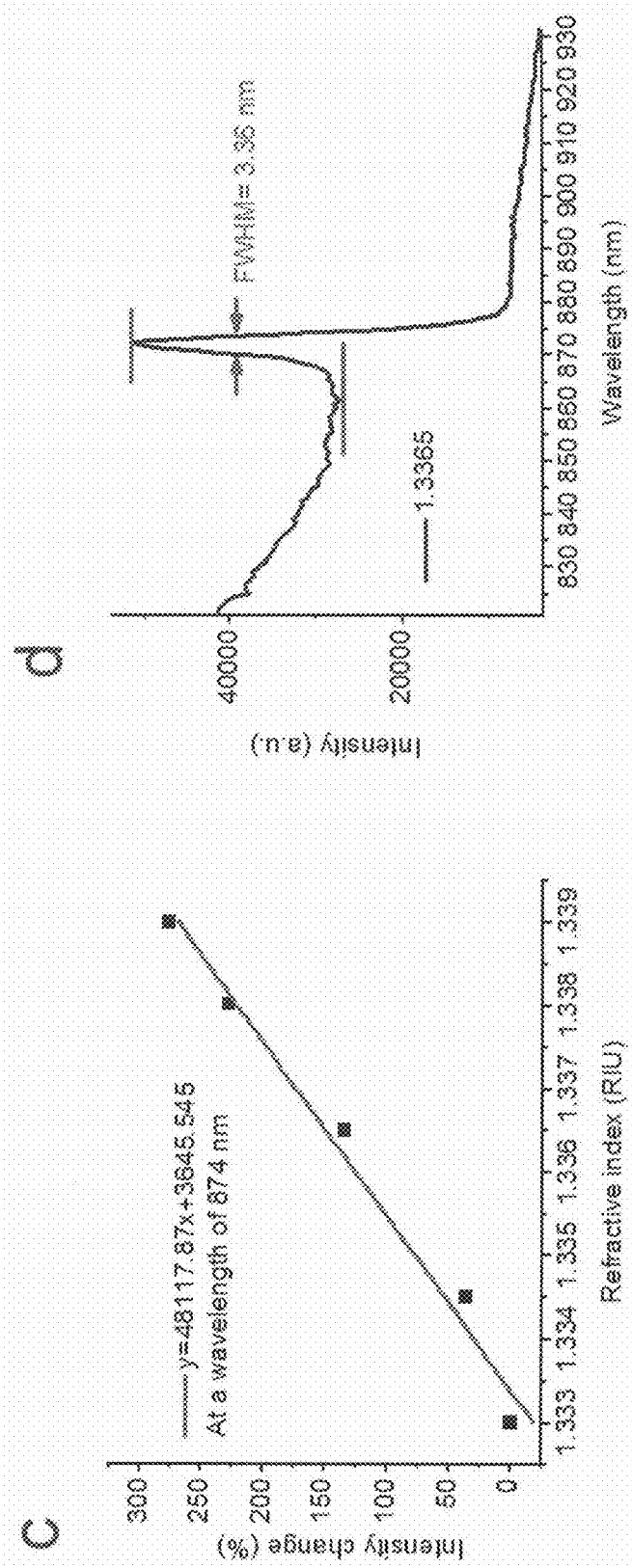

Example 3, Transmission Spectra of the Label-Free Sensing Chip of the Present Invention in Glycerin Solution The extremely sharp and asymmetric Fano resonance profile enhances the sensing sensitivities of SPR sensors. In this example, a variety of water/glycerin mixtures with different concentrations were used as sample solutions (outside medium) in this example. The refractive indexes of the mixtures (from 0 to 15% glycerin) were measured with a refractometer and ranged from 1.333 to 1.384. And, 650-nm-period double-layered metallic nano-ridges (S4) and a normally-incident TM-polarized light were used to detect the transmission spectra, as shown in FIG. 6(a). The wavelength of the Fano resonance at the water/gold interface is near 870 nm when the environmental refractive index (RIU) is 1.3330. The environmental refractive index is the refractive index of the medium covered the metal layer of the present invention. When the concentration of the chemical substance to be determined increases, the environmental refractive index of the sample solution increases, and the wavelength of Fano resonance is red-shifted.

FIG. 6(b) shows the resonant peak wavelength against the refractive index of the sample solution. The slope of the fitting curve of the resonant peak wavelength against the refractive index shows that the refractive index sensitivity is 644 nm/RIU.

FIG. 6(c) shows the normalized intensity change at a wavelength of 874 nm against the refractive index of the outside medium. The slope of the fitting curve shows that the intensity sensitivity is 48117%/RIU. From this figure, it is clear that the measured intensity sensitivity of the present invention is about three times better than the reported intensity sensitivity of prism-based SPR sensors (15000%/RIU) using complicated angular detection method. In other words, the structure of the present invention can achieve a detection limit of $4.15 \times 10^{-6}$ RIU when the intensity resolution of the incident light is fixed at 0.2% (data not shown). The detection limit is calculated by the following formula:

$$\text{Detection limit} = \frac{\text{Intensity stability}}{\text{Intensity sensitivity}} = \frac{0.2\%}{48117\%/RIU} = 4.15 \times 10^{-6}$$

To compare the refractive index sensing capability of the fabricated nanostructures with previous works, we also calculated the figure of merit (FOM) values in wavelength units. The FOM in wavelength units is defined as $S_\lambda/\Delta_\lambda$, where $S_\lambda$ is the wavelength sensitivity and $\Delta_\lambda$ is the resonant width of the plasmon resonance. FIG. 6(d) shows the enlarged intensity spectra of the 650-nm-period double-layered metallic nano-ridges in one of these water/glycerin mixture (n=1.3365) for a normally-incident TM-polarized wave. The measured bandwidth ($\Delta\lambda$) of the Fano resonant peak is 3.36 nm and the wavelength sensitivity is 644 nm/RIU ($S_\lambda$) (see FIG. 6(b)). Thus, the FOM value of 192 is obtained. This value is higher than the theoretically estimated upper limits (FOM=108) of the conventional prism-coupling SPR sensors, the nanohole sensors (FOM=162) and the LSPR sensors (FOM=4.5). The sensing chip of the present invention has a better refractive index sensing capability.

Example 4, Transmission Spectra of the Label-Free Sensing Chip of the Present Invention in Protein Solution A simple optical transmission setup was applied in this example, wherein the sensing chip has a period of nano-ridges of 600 nm (S3). The time-lapsed intensity spectra of the chip were recorded by using a fiber-coupled linear CCD array spectrometer (BWTEK, BTC112E) with a measuring period of 1 min. The sensing chip of the present invention was washed by 10 mM phosphate-buffered saline (PBS, UniRegion Bio-Tech) buffer first (PBS(1)), the solution of 500 μg/mL bovine serum albumin (BSA, Sigma-Aldrich) in PBS (BSA) was added and absorbed on the metal layer of the sensing ship. After washing out the extra BSA by PBS (PBS(2)), the solution of 375 μg/mL anti-BSA (Sigma-Aldrich) in PBS was added into the system and bind the BSA absorbed on the metal layer (anti-BSA). At last, PBS buffer was used to wash the sensing chip again (PBS (3)).

Figure 7:
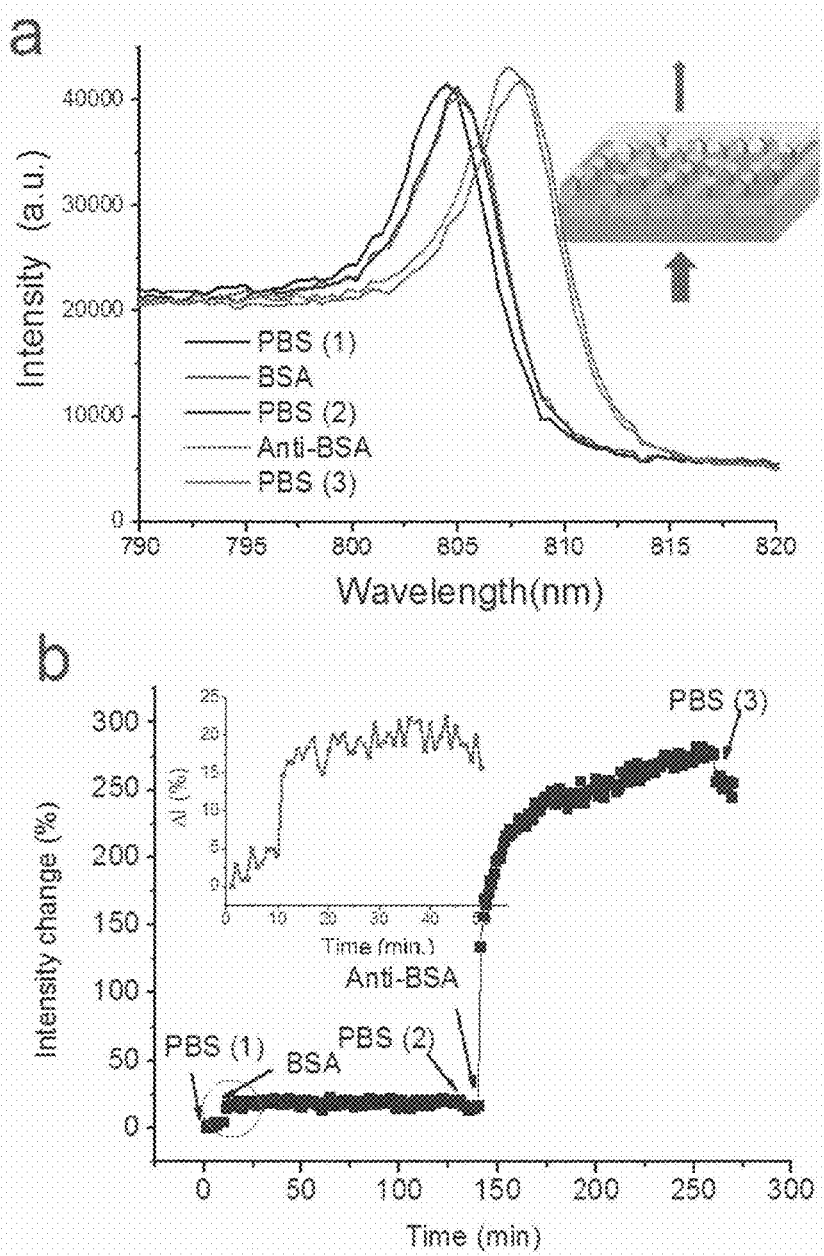
FIG. 7 shows (a) the intensity spectra for different surface conditions with 600-nm-period double-layered metallic nano-ridges; (b) the normalized intensity change at a wavelength of 810 nm as a function of the interaction time for protein-protein interactions. The inset graph shows the partial enlargement of the profile.

FIG. 7(a) shows the measured transmission intensity spectra of for PBS(1), BSA, PBS(2), anti-BSA and PBS (3). Significant changes in wavelength shift and transmitted intensity are observed in the profiles of BSA and anti-BSA. The monolayer BSA bound on the surface of the gold layer results in a 0.40-nm red shift. The 150-kDa-sized anti-BSA resulted in a 2.76-nm wavelength shift. FIG. 7(b) shows the normalized intensity change at a wavelength of 810 nm as a function of the interaction time for protein-protein interactions. Because the highest intensity sensitivity for the chip with a period of 600 nm is at the wavelength of 810 nm, the measured spectra were analyzed at this wavelength. The BSA coated on the gold surface resulted in an intensity change of 17%. The Anti-BSA with larger molecular weight caused an intensity change up to 237%, which is better than the intensity change (12%) of nanoslit arrays. The intensity sensitivity is about 4000%/RIU for nanoslit arrays.

Different periodic ridges (S5-S10) having a variety of widths were tested in the above-mentioned examples. These periodic ridges also gave good results (data not shown).

The proposed double-layered metallic nano-ridges can generate extremely sharp and asymmetric Fano resonances in transmission spectra. Such a resonance has a narrower band width which can enhance the sensing sensitivities of SPR sensors and effectively improve the sensing resolution. For commercial applications, the label-free biochips can be applied to specific molecular binding events, concentration analysis, affinity analysis, dynamic analysis and high-throughput detection.

What is claimed is:

1. A label-free sensing chip comprising:
   (a) a transparent substrate comprising a base and first periodic ridges; and
   (b) a metal layer covering said transparent substrate, wherein the metal layer comprises second periodic ridges and third periodic ridges, in which said second periodic ridges has a height equal to or greater than the height of the first periodic ridges, and each ridge of the second periodic ridges fits into the space between each ridge of the first periodic ridges, and said third periodic ridges located on said first periodic ridges,
   wherein said second periodic ridges and said third periodic ridges form cavities to generate Fano resonances by coupling Bloch wave surface plasmon polaritons (BW-SPPs) and localized surface plasmon resonances (LSPRs).

2. The label-free sensing chip according to claim 1, further comprising a molecule layer coated on the metal layer, wherein said molecule layer comprises one or more molecules for binding the chemical substance.

3. The label-free sensing chip according to claim 2, wherein said chemical substance comprises elements, biomolecules, polymers and drugs.

4. The label-free sensing chip according to claim 3, wherein said biomolecules comprise proteins, DNA, RNA.

5. The label-free sensing chip according to claim 1, wherein said second periodic ridges have a height of several tens nm to several hundred nm.

6. The label-free sensing chip according to claim 1, wherein said second periodic ridges have a period of several hundred nm to several μm.

7. The label-free sensing chip according to claim 6, wherein each ridge of said first periodic ridges has a width of 10 nm to 200 nm.

8. The label-free sensing chip according to claim 1, wherein said transparent substrate is composed of glass or a plastic material.

9. The label-free sensing chip according to claim 8, wherein said transparent substrate is composed of the plastic material and said plastic material is selected from acrylic, UV gel, polycarbonate or cyclo olefin polymers.

10. The label-free sensing chip according to claim 1, wherein said metal layer is composed of the metal selected from gold, silver, aluminum or copper.

11. The label-free sensing chip according to claim 10, wherein said metal is gold.

12. A method for identifying a chemical substance, comprising:
    (a) providing a sample of said chemical substance;
    (b) adding said sample solution on the label-free sensing chip according to claim 1 to cover the metal layer;
    (c) transmitting an incident light from the substrate side;
    (d) detecting the transmission spectra of the sample to identify the chemical substance.

13. The method according to claim 12, wherein said label-free sensing chip further comprises a molecule layer coated on the metal layer, and said molecule layer comprises one or more molecules for binding the chemical substance.

14. The method according to claim 13, further comprising a step after said step (b): interacting the one or more molecules and the chemical substance.

15. The method according to claim 12, wherein said sample is in form of liquid or gas.

16. The method according to claim 13, wherein said chemical substance comprises biomolecules.

17. The method according to claim 16, wherein said biomolecules comprise proteins.

18. The method according to claim 17, wherein said protein is solved in a PBS buffer solution.

19. The method according to claim 13, wherein said incident light is polarized.

20. The method according to claim 13, wherein said incident light is transmitted into the substrate in direction substantively perpendicular to the label-free sensing chip.

* * * * *